(12) United States Patent
Nicholas

(10) Patent No.: US 11,802,609 B2
(45) Date of Patent: Oct. 31, 2023

(54) HANDLE ASSEMBLIES FOR HAND-HELD SURGICAL INSTRUMENTS

(71) Applicant: Covidien LP, Mansfield, MA (US)

(72) Inventor: David A. Nicholas, Trumbull, CT (US)

(73) Assignee: COVIDIEN LP, Mansfield, MA (US)

(*) Notice: Subject to any disclaimer, the term of this patent is extended or adjusted under 35 U.S.C. 154(b) by 320 days.

(21) Appl. No.: 17/121,843

(22) Filed: Dec. 15, 2020

(65) Prior Publication Data

US 2022/0186815 A1 Jun. 16, 2022

(51) Int. Cl.
| | | |
|---|---|---|
| *F16H 1/22* | (2006.01) | |
| *A61B 17/072* | (2006.01) | |
| *A61B 17/115* | (2006.01) | |
| *A61B 17/00* | (2006.01) | |

(52) U.S. Cl.
CPC ............. *F16H 1/22* (2013.01); *A61B 17/072* (2013.01); *A61B 17/1155* (2013.01); *A61B 2017/00398* (2013.01); *A61B 2017/00486* (2013.01); *A61B 2017/00734* (2013.01)

(58) Field of Classification Search
CPC ..... F16H 1/22; A61B 17/072; A61B 17/1155; A61B 2017/00398; A61B 2017/00486; A61B 2017/00734
USPC .................................................. 74/325, 331
See application file for complete search history.

(56) References Cited

U.S. PATENT DOCUMENTS

| | | | |
|---|---|---|---|
| 9,510,827 B2 * | 12/2016 | Kostrzewski | A61B 17/068 |
| 9,517,065 B2 * | 12/2016 | Simms | A61B 17/0682 |
| 9,826,976 B2 | 11/2017 | Parihar et al. | |
| 10,405,857 B2 | 9/2019 | Shelton | |
| 10,610,313 B2 | 4/2020 | Bailey et al. | |
| 2016/0249915 A1 * | 9/2016 | Beckman | A61B 17/1155 |
| | | | 227/175.1 |
| 2016/0310134 A1 * | 10/2016 | Contini | A61B 17/0686 |
| 2016/0324514 A1 * | 11/2016 | Srinivas | A61B 17/00234 |
| 2016/0324518 A1 * | 11/2016 | Nicholas | A61B 17/068 |
| 2016/0345973 A1 * | 12/2016 | Marczyk | A61B 17/07207 |
| 2016/0374678 A1 * | 12/2016 | Becerra | A61B 17/07207 |
| | | | 227/177.1 |
| 2017/0175852 A1 | 6/2017 | Nicholas | |
| 2020/0000463 A1 | 1/2020 | Whitman et al. | |

FOREIGN PATENT DOCUMENTS

EP 3488801 A1 5/2019

OTHER PUBLICATIONS

Extended European Search Report dated May 10, 2022, issued in corresponding EP Application No. 21214081, 12 pages.

* cited by examiner

*Primary Examiner* — Ha Dinh Ho
(74) *Attorney, Agent, or Firm* — CARTER, DELUCA & FARRELL LLP

(57) ABSTRACT

A handle assembly includes a single-motor transmission assembly for actuating various functions of an attached end effector.

9 Claims, 4 Drawing Sheets

HANDLE ASSEMBLIES FOR HAND-HELD SURGICAL INSTRUMENTS

BACKGROUND

1. Technical Field

The disclosure relates to surgical instruments. More specifically, the disclosure relates to handle assemblies including a single-motor transmission for actuating a variety of functions of surgical attachments.

2. Background of Related Art

Electromechanical surgical instruments include a reusable handle assembly and disposable loading units and/or single use loading units, such as, for example, surgical end effectors. The end effectors are selectively connected to the handle assembly prior to use and then disconnected from the handle assembly following use in order to be disposed of or in some instances sterilized for re-use. There are one or more drive mechanisms within the handle assembly for carrying out the various functions of the end effector.

SUMMARY

In one aspect of the disclosure, a transmission assembly for use in a hand-held surgical instrument is provided and includes a housing, a main drive motor supporting a main drive gear, first and second output gears operably coupled to the main drive gear and configured to rotate in response to a rotation of the main drive gear, first and second output shafts rotatably supported in the housing, and a selector cam associated with the first and second output shafts. The selector cam is configured to move between a first position and a second position. In the first position, the selector cam non-rotatably couples the first output shaft to the first output gear and the second output gear is rotatable relative to the second output shaft. In the second position, the selector cam non-rotatably couples the second output shaft to the second output gear and the first output gear is rotatable relative to the first output shaft.

In aspects, the transmission assembly may further include a first coupling shaft non-rotatably coupled to the first output shaft and a second coupling shaft non-rotatably coupled to the second output shaft. The first coupling shaft may be configured to non-rotatably engage the first output gear when the selector cam is in the first position such that only the first output shaft of the first and second output shafts rotates in response to the rotation of the main drive gear. The second coupling shaft may be configured to non-rotatably engage the second output gear when the selector cam is in the second position such that only the second output shaft of the first and second output shafts rotates in response to the rotation of the main drive gear.

In aspects, the first coupling shaft may extend through the first output gear and may be slidable in the first output gear between a proximal position and a distal position. In the proximal position, the first coupling shaft may be non-rotatably engaged with the first output gear. In the distal position, the first coupling shaft may be disengaged from the first output gear.

In aspects, the first coupling shaft may have a proximal end portion engaged with the selector cam, and a distal end portion having a gear. The first output gear may have a geared inner surface configured to meshingly engage with the gear of the distal end portion of the first coupling shaft when the first coupling shaft is in the proximal position.

In aspects, the selector cam may have a distal-facing surface engaged to the first and second coupling shafts. The distal-facing surface of the selector cam may have a recess in which a proximal end portion of the first coupling shaft is received when the selector cam is in the first position.

In aspects, the selector cam may have an arcuate shape and may be configured to rotate around the main drive motor between the first and second positions.

In aspects, the distal-facing surface of the selector cam may have a first ramped end portion, and an opposite second ramped end portion.

In aspects, the first and second coupling shafts may each be resiliently biased toward the proximal position. The selector cam may be configured to selectively maintain only one of the first or second coupling shafts in the distal position.

In aspects, the transmission assembly may further include a third output shaft and a third output gear operably coupled to the main drive gear. The selector cam may be configured to move to a third position, in which the first and second output shafts are disengaged from the respective first and second output gears and the third output shaft is non-rotatably engaged to the third output gear.

In aspects, the transmission assembly may further include a selector motor supporting a gear that is operably coupled to the selector cam. The selector motor may be configured to move the selector cam between the first and second positions.

In aspects, the selector cam may have a plurality of teeth in meshing engagement with the gear of the selector motor.

In accordance with another aspect of the disclosure, a handle assembly for operating a surgical end effector is provided and includes a handle housing and a transmission assembly. The handle housing has a barrel portion and a handle portion extending from the barrel portion. The transmission assembly is supported in the barrel portion of the handle housing and includes a main drive motor having a main drive gear, first, second, and third output shafts, first, second, and third output gears operably coupled to the main drive gear and configured to rotate in response to a rotation of the main drive gear, a selector cam, and a selector motor operably coupled to the selector cam. The selector motor is configured to move the selector cam relative to the first, second, and third output shafts between a first position and a second position. In the first position, the first output shaft is non-rotatably coupled to the first output gear. In the second position, the second output shaft is non-rotatably coupled to the second output gear. In the third position, the third output shaft is non-rotatably coupled to the third output gear.

In aspects, the transmission assembly may further include a first coupling shaft non-rotatably coupled to the first output shaft, a second coupling shaft non-rotatably coupled to the second output shaft, and a third coupling shaft non-rotatably coupled to the third output shaft.

In aspects, the first coupling shaft may be configured to translate into non-rotatable engagement with the first output gear when the selector cam is moved to the first position such that only the first output shaft rotates in response to a rotation of the main drive gear when the selector cam is in the first position.

In aspects, the second coupling shaft may be configured to translate into non-rotatable engagement with the second output gear when the selector cam is moved to the second position such that only the second output shaft rotates in response to the rotation of the main drive gear when the selector cam is in the second position.

In aspects, the third coupling shaft may be configured to translate into non-rotatable engagement with the third output gear when the selector cam is moved to the third position such that only the third output shaft rotates in response to the rotation of the main drive gear when the selector cam is in the third position.

In aspects, the first, second, and third coupling shafts may each be resiliently biased toward a proximal position in which the first, second, and third coupling shafts are respectively non-rotatably engaged with the first, second, and third output gears.

In aspects, the selector cam may be configured to selectively maintain only one of the first, second, or third coupling shafts in a distal position and out of non-rotatable engagement with the respective first, second, and third output gears.

In aspects, the selector cam may have a distal-facing surface configured to engage and maintain a selected one of the first, second, or third coupling shafts in the distal position.

In aspects, the transmission assembly may further include a first coupling shaft non-rotatably coupled to the first output shaft. The first coupling shaft may be configured to translate into non-rotatable engagement with the first output gear when the selector cam is moved to the first position such that only the first output shaft rotates in response to a rotation of the main drive gear when the selector cam is in the first position.

In aspects, the first coupling shaft may extend through the first output gear and may be slidable therein between a proximal position and a distal position. In the proximal position, the first coupling shaft is non-rotatably engaged with the first output gear. In the distal position, the first coupling shaft is disengaged from the first output gear.

In aspects, the first coupling shaft may have a proximal end portion engaged with the selector cam, and a distal end portion having a gear. The first output gear may have a geared inner surface configured to meshingly engage with the gear of the distal end portion of the first coupling shaft when the first coupling shaft is in the proximal position.

In aspects, the selector motor may rotatably support and drive a gear. The selector cam may have a plurality of teeth in meshing engagement with the gear of the selector motor. The teeth of the selector cam may be configured to move the selector cam between the first, second, and third positions.

In aspects, the selector cam may have an arcuate shape and may be configured to rotate around the main drive motor between the first, second, and third positions.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the disclosure are described herein with reference to the accompanying drawings, wherein.

DETAILED DESCRIPTION

Figure 1:
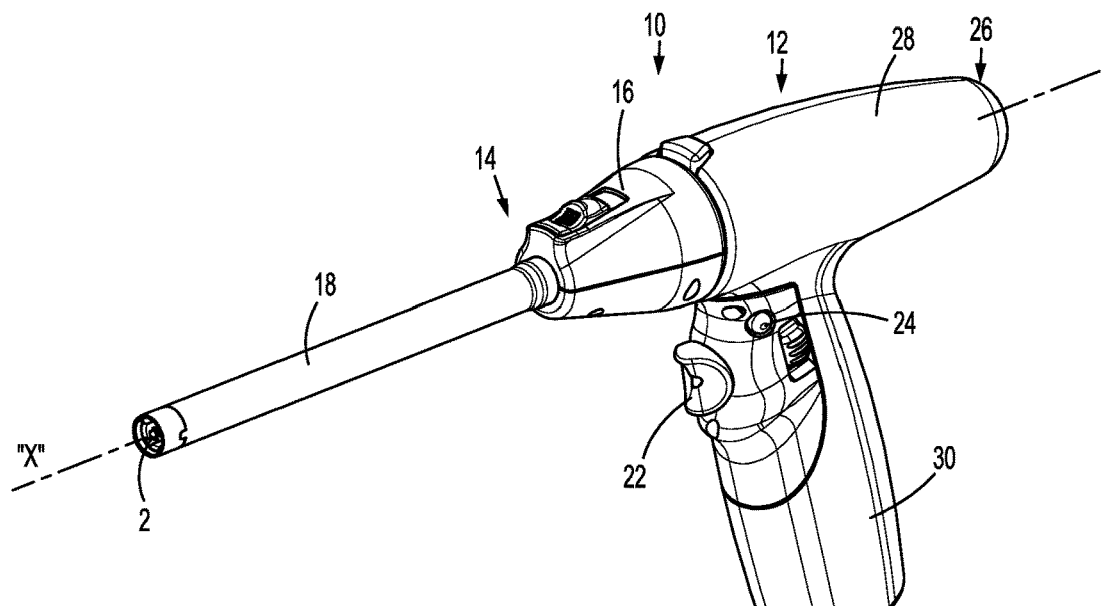
FIG. 1 is a perspective view of a hand-held electromechanical surgical instrument including a handle assembly and an adapter assembly coupled to the handle assembly, in accordance with an embodiment of the disclosure.

Embodiments of the presently disclosed surgical instruments are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

This disclosure is directed to a transmission assembly disposable within a handle housing of a hand-held surgical instrument. The transmission assembly has a single motor that drives a plurality of output shafts, which are configured to transmit rotational motion to corresponding driven elements of a surgical end effector. The transmission assembly includes a selector cam that selectively operably couples a single output shaft with the motor. When a user depresses a switch, a computer processor within the handle housing determines the desired user request and positions the selector cam in the appropriate position to operate the desired output shaft.

The main advantage of a single motor design is the elimination of motors due to the simple shaft selectable transmission. This transmission design provides the same device performance as a multiple motor design with the advantages of allowing the product to be manufactured at a lower cost. Further, the ergonomics are improved because the physical size and weight of the device will be less and will require fewer electrical components and circuitry which contributes to improved reliability.

Figure 2:
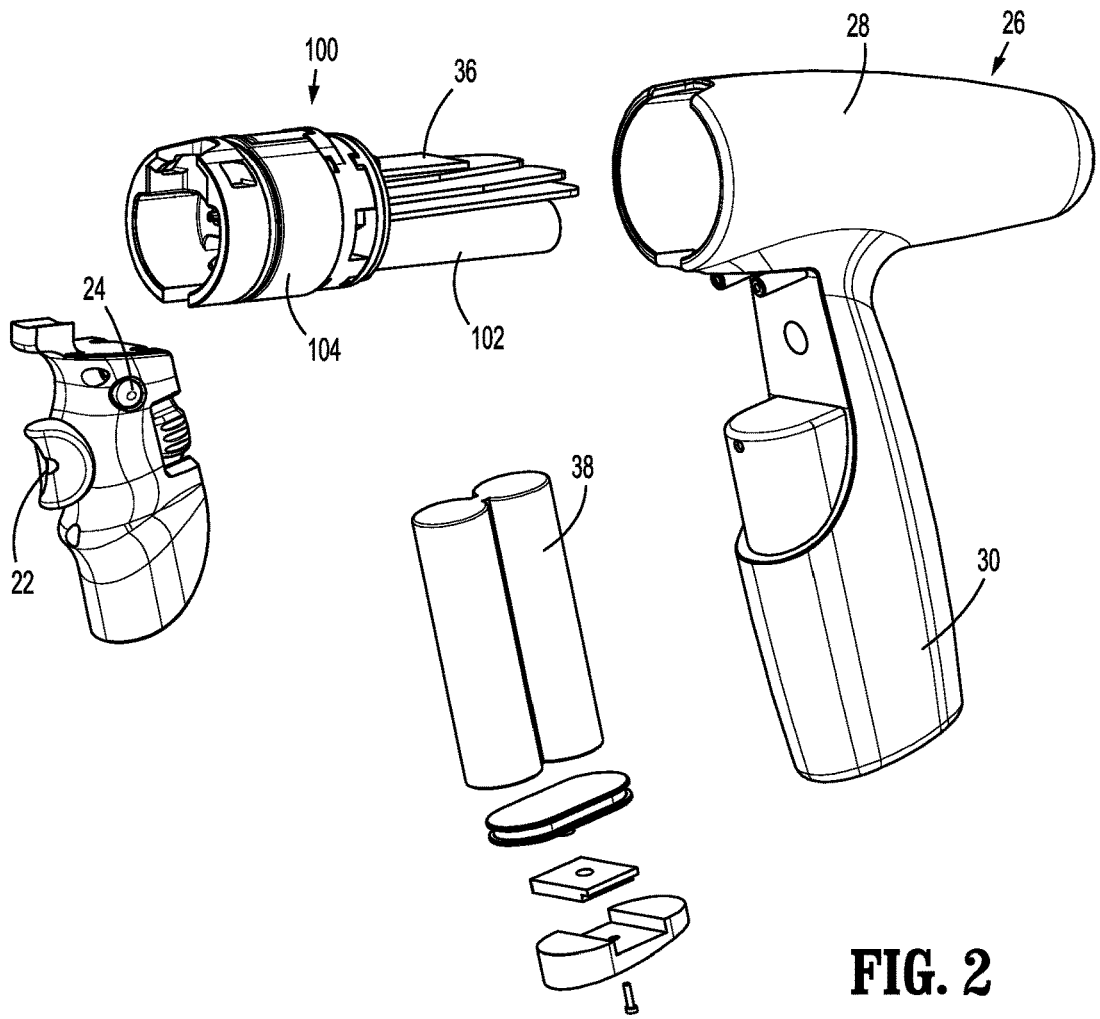
FIG. 2 is a perspective view, with parts separated, illustrating the handle assembly of FIG. 1.
Figure 3:
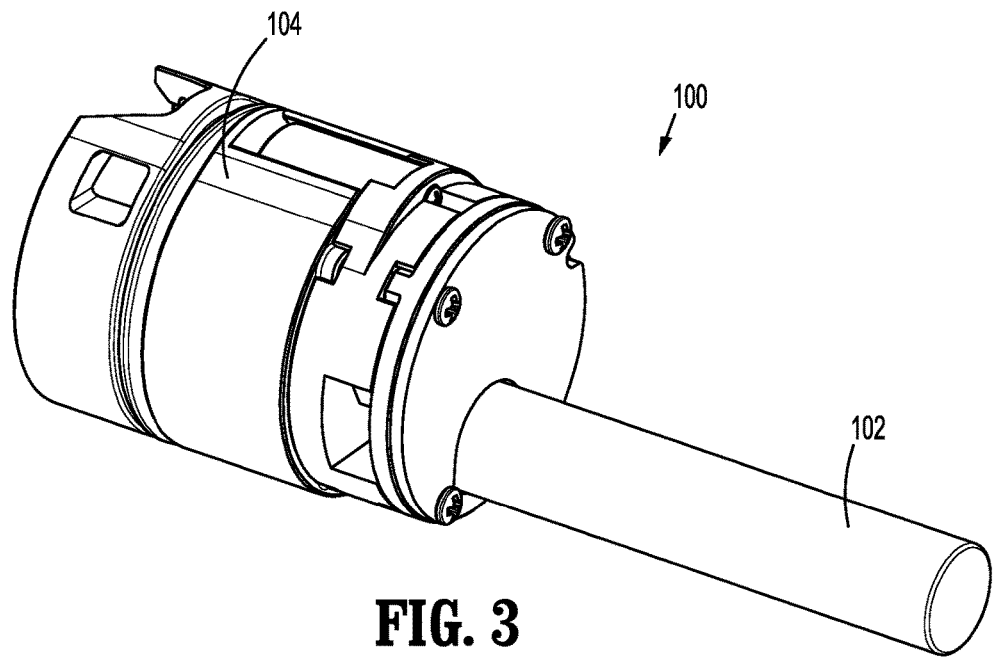
FIG. 3 is a side, perspective view illustrating a transmission assembly of the handle assembly of FIG. 2.
Figure 4:
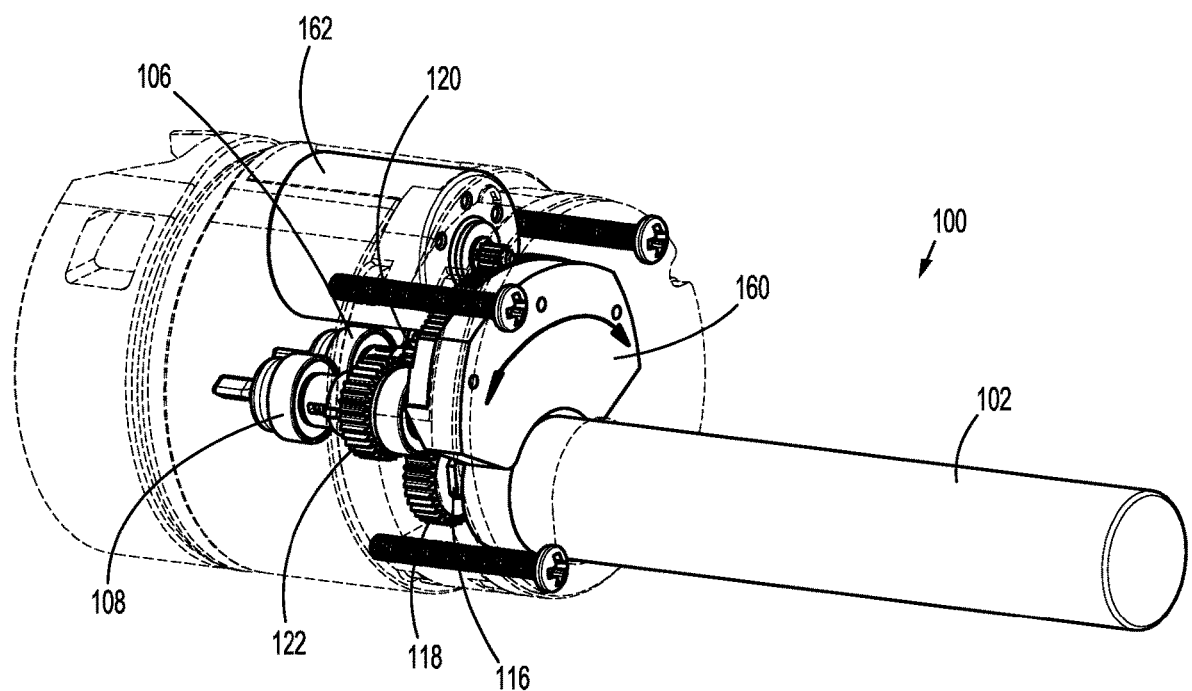
FIG. 4 is a side, perspective view, illustrating internal components of the transmission assembly of FIG. 3.

With reference to FIGS. 1 and 2, a surgical instrument, in accordance with an embodiment of the disclosure, is generally designated as 10, and is in the form of a powered hand-held electromechanical surgical instrument configured for selective coupling thereto of a plurality of different surgical end effectors (not explicitly shown), for example, a linear surgical stapler end effector, a circular stapler end effector, a hernia tack end effector, or the like. An exemplary end effector configured for actuation and manipulation by the powered hand-held electromechanical surgical instrument 10 may be found at least in U.S. Pat. No. 8,011,555, the entire contents of which being incorporated by reference herein.

The hand-held electromechanical surgical instrument 10 includes a handle assembly 12 and an adapter assembly 14 extending distally from the handle assembly 12. The adapter assembly 14 has a knob housing 16 coupled to the handle assembly 12 and a shaft portion 18 configured for selective connection with a selected surgical end effector. The knob housing 16 may be rotatably coupled to the handle assembly 12 and configured to be manually rotated about a longitudinal axis "X" defined by the shaft portion 18 to rotate the end effector.

The handle assembly 12 includes a handle housing 26 consisting of a barrel portion 28 substantially aligned with the longitudinal axis "X," and a handle portion 30 extending perpendicularly downward from the barrel portion 28. The handle assembly 12 includes a printed circuit board or processor 36 and a battery 38 disposed in the handle housing 26. The printed circuit board 36 is configured to be in electrical communication with the battery 38 and a main drive motor 102 of a transmission assembly 100. The main drive motor 102 may be wirelessly connected, connected via a wire, or otherwise electrically connected to the printed circuit board 36 and the battery 38. The handle assembly 12 also has a fire switch 22 configured to actuate the various functions of the end effector and a safety switch 24 for preventing an inadvertent actuation of the fire switch 22. The fire switch 22 may be a finger switch pivotably coupled to the handle portion 30 in communication with the printed circuit board 36 for activating the battery 38 to ultimately actuate an open/close and staple firing function of the end effector.

With reference to FIGS. 3-8, the transmission assembly 100 of the handle assembly 12 is configured for removable receipt in the barrel portion 28 of the handle housing 26 and generally includes a body portion or housing 104, the main drive motor 102, a plurality of output shafts 106, 108, 110, a selector cam 160, and a selector motor 162. The main drive motor 102 of the transmission assembly 100 may be an electric motor and rotatably supports a drive shaft 116 about which a main drive gear 118, such as, for example, a spur gear, is non-rotatably fixed. As such, an actuation of the main drive motor 102 results in a rotation of the main drive gear 118. In aspects, the main drive motor 102 may be considered separate from the transmission assembly 100.

The output shafts 106, 108, 110 are configured to be selectively driven by the main drive motor 102 whereby the selected output shaft 106, 108, or 110 rotates to transmit its rotational motion to a driven element (e.g., drive shaft 2 of adapter assembly 14 of FIG. 1) to ultimately effect a corresponding function of the attached surgical end effector. The output shafts 106, 108, 110 are rotatably supported in the transmission housing 104 and are resisted from sliding within the transmission housing 104 by seals 112. Each of the output shafts 106, 108, 110 has a distal end 114 configured to non-rotatably couple to the respective driven element of the adapter assembly 14.

With reference to FIGS. 4-8, the transmission assembly 100 further includes a plurality of output gears, such as, first, second, and third output spur gears 120, 122, 124 rotationally supported in the transmission housing 104 and about the respective output shafts 106, 108, 110. The output gears 120, 122, 124 are rotatably supported about the respective output shafts 106, 108, 110 such that the output gears 120, 122, 124 are permitted to rotate relative to and about the output shafts 106, 108, 110. The first or intermediate output gear 120 is in direct meshing engagement with the main drive gear 118, whereas the second and third output gears 122, 124 are operably coupled to the main drive gear 118 via the first output gear 120. In this way, an actuation of the main drive motor 102 results in the simultaneous rotation of each of the first, second, and third output gears 120, 122, 124.

The transmission assembly 100 further includes a plurality of coupling shafts, such as, for example, first, second, and third coupling shafts 130, 132, 134 configured to operable couple the respective first, second, and third output gears 120, 122, 124 to the first, second, and third output shafts 106, 108, 110, as will be described. The coupling shafts 130, 132, 134 are each disposed in a respective hollow interior of the output shafts 106, 108, 110 and are slidable therein along a longitudinal axis of the output shafts 106, 108, 110 (e.g., as illustrated by double headed arrow of FIG. 6) between a proximal position and a distal position. The transmission assembly 100 may include a plurality of biasing members, such as, for example, first second, and third coil springs 136, 138, 140 configured to resiliently bias the coupling shafts 130, 132, 134 relative to the output shafts 106, 108, 110 toward the proximal position. Each of the coupling shafts 130, 132, 134 has a tab or protrusion 142 (FIGS. 7-8) that extends through a slit 144 defined in each of the output shafts 106, 108, 110 such that the first, second, and third output shafts 106, 108, 110 rotate with and by a rotation of the respective first, second, and third coupling shafts 130, 132, 134.

Each of the coupling shafts 130, 132, 134 has a proximal end portion 150a (FIG. 6) that protrudes proximally from the respective output shafts 106, 108, 110 and the transmission housing 104, and a distal end portion 150b received in the respective output shaft 106, 108, 110. The distal end portion 150b of each of the coupling shafts 130, 132, 134 has a gear 152 formed therewith or fixed thereabout, and each of the output gears 120, 122, 124 has an inner geared surface 154 configured to meshingly engage with the respective gear 152 of the coupling shaft 130, 132, 134 when a selected one of the coupling shafts 130, 132, 134 is in the proximal position. As such, when the selected coupling shaft 130, 132, or 134 is in the proximal position, rotation of the corresponding output gear 120, 122, or 124 drives a corresponding rotation of the selected coupling shaft 130, 132, or 134 and, in turn, drives a rotation of the corresponding output shaft 106, 108, or 110. On the other hand, when the selected coupling shaft 130, 132, or 134 is in the distal position, the gear 152 of the selected coupling shaft 130, 132, or 134 is disengaged from the geared inner surface 154 of the respective output gear 120, 122, or 124 so that rotation of the output gear 120, 122, 124 does not result in a concomitant rotation of the coupling shaft 130, 132, 134 or the output shaft 106, 108, 110.

With continued reference to FIGS. 4-8, the selector cam 160 of the transmission assembly 100 is operably coupled to the selector motor 162 and is configured to maintain only one of the coupling shafts 130, 132, or 134 in operable engagement with the main drive motor 102 at a time. The selector motor 162 may be an electric stepper motor and rotatably supports a gear 164. The selector cam 160 has a generally arcuate shape and is disposed about the main drive motor 102. The selector cam 160 has an outer circumferential edge 166 having a plurality of teeth 168 in meshing engagement with the gear 164 of the selector motor 162 such that actuation of the selector motor 162 moves the selector cam 160 about the main drive motor 102 between a plurality of discrete positions.

Figure 5:
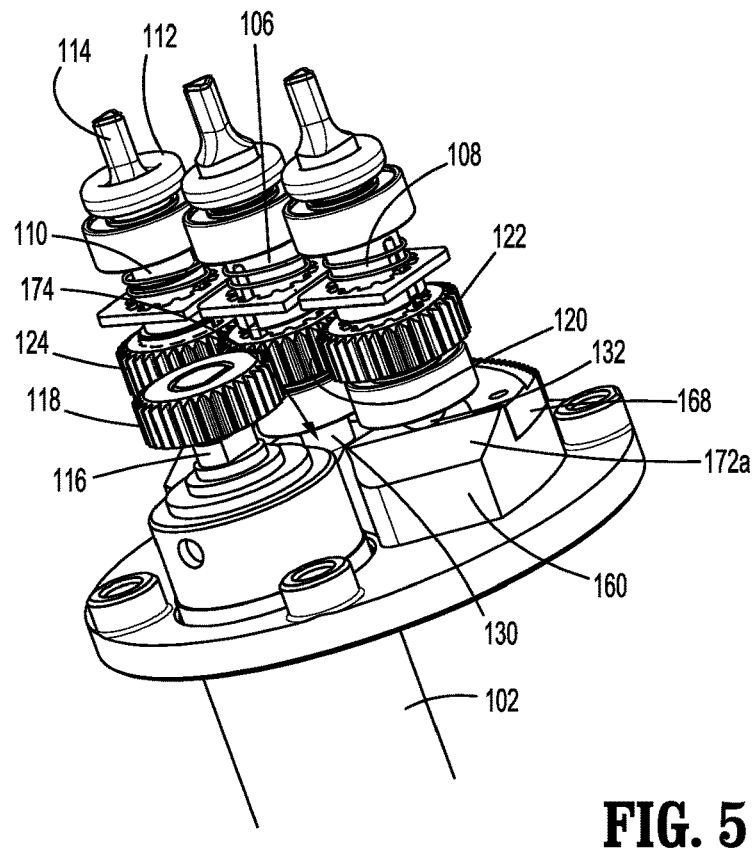
FIG. 5 is a perspective view illustrating the internal components of the transmission assembly of FIG. 4.
Figure 6:
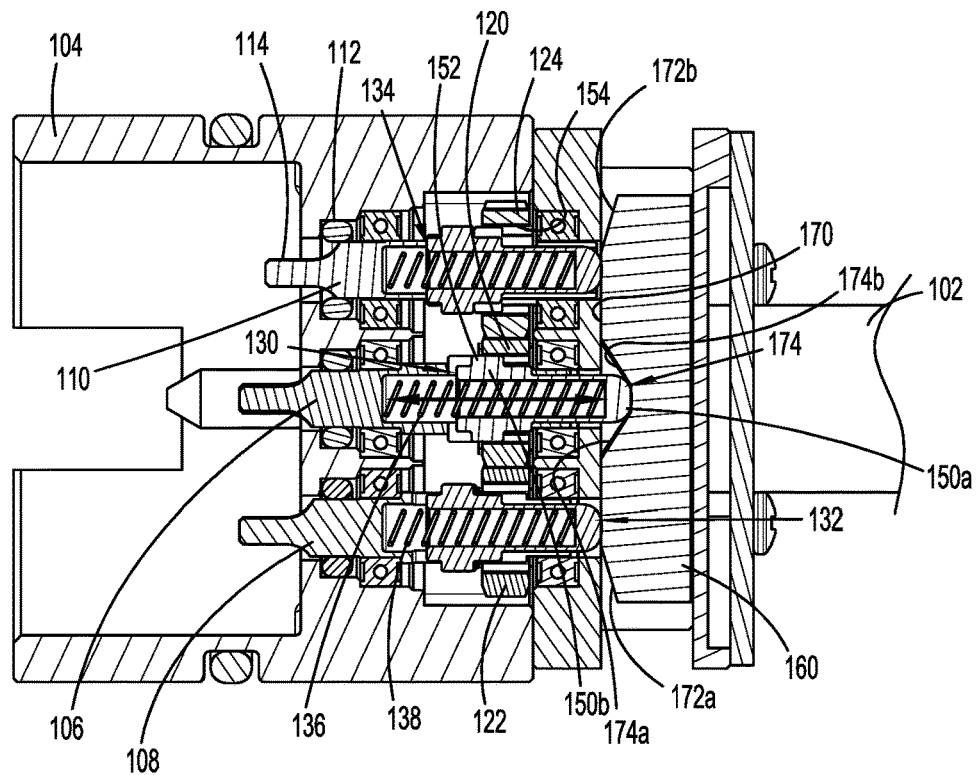
FIG. 6 is a cross-sectional view illustrating the internal components of the transmission assembly of FIG. 4.

As best shown in FIGS. 5-6, the selector cam 160 has a distal-facing surface 170 engaged with the proximal end portion 150a of each of the coupling shafts 130, 132, 134. The distal-facing surface 170 of the selector cam 160 has opposing first and second ramped end portions 172a, 172b and a recess 174 disposed centrally between the first and second ramped end portions 172a, 172b. The recess 174 is defined by a pair of ramped segments 174a, 174b of the distal-facing surface 170. The selector cam 160, in response to an actuation of the selector motor 162, is configured to move along an arcuate path between a first position (FIG. 4), a second position, and a third position (e.g., as illustrated by double-headed arrows of FIGS. 4 and 7).

When the selector cam 160 is in the first position, the first or central coupling shaft 130 is aligned with the recess 174 and therefore in the proximal position, and the second and third coupling shafts 132, 134 are maintained in the distal position by the distal-facing surface 170 of the selector cam 160. When the selector cam 160 is in the second position (not explicitly shown), the second coupling shaft 132 is disposed out of alignment with the distal-facing surface 170 of the selector cam 160 and therefore in the proximal position, and the first and third coupling shafts 130, 134 are maintained in the distal position by the distal-facing surface 170. When the selector cam 160 is in the third position (not explicitly shown), the third coupling shaft 134 is out of alignment with the distal-facing surface 170 and therefore in the proximal position, and the first and second coupling shafts 130, 132 are maintained in the distal position by the distal-facing surface 170.

Figure 7:
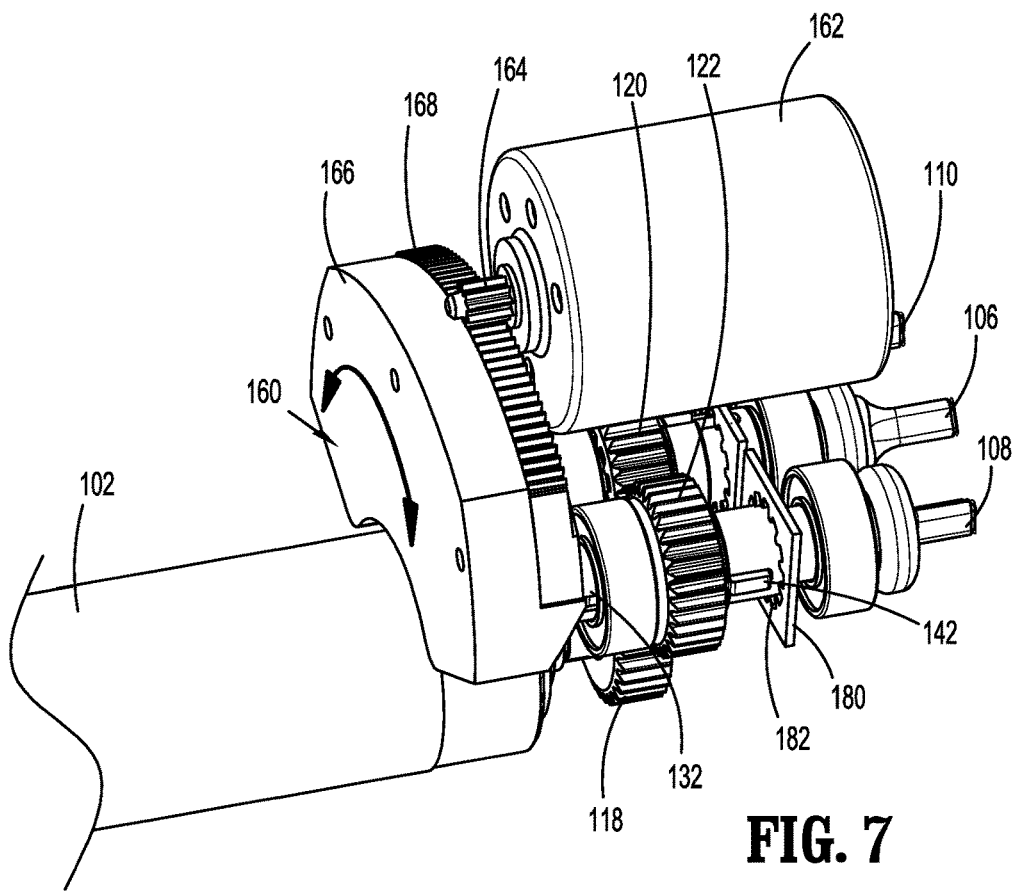
FIG. 7 is a side, perspective view illustrating a selector cam and a selector motor of the transmission assembly of FIG. 4.
Figure 8:
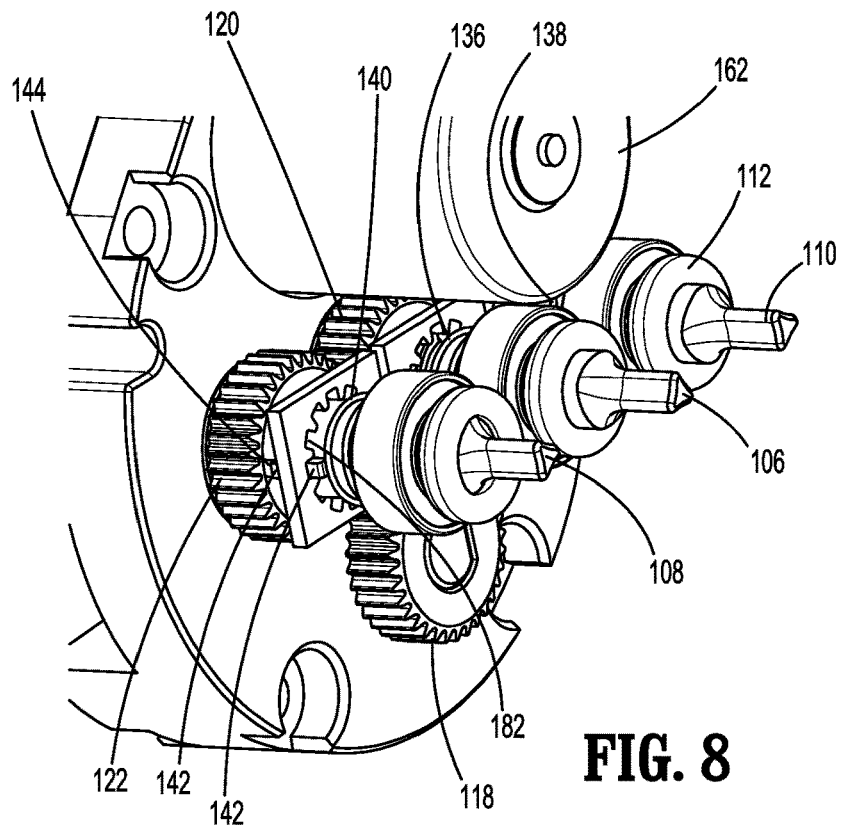
FIG. 8 is an enlarged perspective view illustrating a shaft lockout of the transmission assembly of FIG. 4.

With brief reference to FIGS. 7-8, the transmission assembly 100 may further include a bracket 180 disposed about each of the output shafts 106, 108, 110 and fixed within the transmission housing 104. The bracket 180 defines a plurality of apertures 182 configured for receipt of the tab 142 of the respective coupling shafts 130, 132, 134 when the coupling shafts 130, 132, 134 are in the distal position. With the tab 142 of each the coupling shafts 130, 132, 134 received in the respective aperture 182 of the bracket 180, inadvertent rotation of the coupling shafts 130, 132, 134, and therefore the respective output shafts 106, 108, 110, is resisted.

In operation, a user may manually select the desired function of the end effector to be carried out by the handle assembly 12. For example, a user may desire for an opening/closing of the attached end effector. The processor 36 (FIG. 2) of the handle assembly 12 translates this command into an appropriate operation of the first or central output shaft 106 of the transmission assembly 100. To enable operation of the first output shaft 106, the processor 36 actuates the selector motor 162 to move the selector cam 160 into the first position, as shown in FIGS. 5 and 6. As the selector cam 160 is moved toward the first position, in response to an activation of the selector motor 162, the recess 174 in the distal-facing surface 170 of the selector cam 160 moves into alignment with the first coupling shaft 130 of the transmission assembly 100 whereby the resilient bias of the biasing member 136 is allowed to drive the first coupling shaft 130 into the proximal position. In the proximal position, the proximal end portion 150a of the first coupling shaft 130 is received in the recess 174 of the selector cam 160. With the selector cam 160 in the first position, the second and third coupling shafts 132, 134 are maintained in their distal positions by the distal-facing surface 170 of the selector cam 160.

With the selector cam 160 in the selected first position, the handle assembly 12 may generate an indication (e.g., an auditory or visual indication) to the user that the handle assembly 12 is ready to be actuated to perform the desired function. A user may then actuate the fire switch 22 (FIG. 1) of the handle assembly 12, whereby the main drive motor 102 drives a rotation of the main drive gear 118, which drives a concomitant rotation of each of the output gears 120, 122, 124. However, since only the first coupling shaft 130 of the plurality of coupling shafts 130, 132, 134 is in the proximal position with the selector cam 160 being set in the first position, only the first coupling shaft 130 is operably engaged with the main drive gear 118. In particular, the gear 152 (FIG. 6) of the first coupling shaft 130 is in meshing engagement with the geared inner surface 154 of the first output gear 120 such that the rotation of the first output gear 120 results in rotation of the first coupling shaft 130 and, in turn, rotation of the first output shaft 106. In contrast, the second and third output shafts 108, 110 remain stationary given that the gear 152 of the respective second and third coupling shafts 132, 134 is distal and out of engagement with the respective second and third output gears 122, 124.

If a user desires that another type of function of the end effector be carried out by the handle assembly 12, the selector cam 160 may be moved to the corresponding position, for example, the second position. As the selector cam 160 is moved from the first position to the second position (e.g., as illustrated by double-headed arrows of FIGS. 4 and 7), the ramped segment 174a of the distal-facing surface 170 of the selector cam 160 distally drives the first coupling member 130 from the proximal position toward the distal position against the resilient bias of the biasing member 136 (e.g., as illustrated by double headed arrow of FIG. 6). With the selector cam 160 in the second position, the distal-facing surface 170 of the selector cam 160 maintains the third coupling member 134 in the distal position. Simultaneously, the distal-facing surface 170 of the selector cam 160 moves out of alignment with the second coupling member 132 (e.g., the selector cam 160 is disengaged from the second coupling member 132) to allow the second coupling member 132 to move to the proximal position in which the gear 152 of the second coupling member 132 engages the geared inner surface 154 of the second output gear 122. In this configuration, an activation of the main drive motor 102 ultimately results in the rotation of only the second output shaft 108 among the plurality of output shafts 106, 108, 110.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed surgical instruments including switch assemblies. Therefore, the above description should not be construed as limiting, but merely as exemplifications of embodiments. Those skilled in the art will envision other modifications within the scope and spirit of the disclosure.

The invention claimed is:
1. A handle assembly for operating a surgical end effector, the handle assembly comprising:
   a handle housing having a barrel portion, and a handle portion extending from the barrel portion; and
   a transmission assembly supported in the barrel portion of the handle housing and including:
      a main drive motor having a main drive gear;
      first, second, and third output shafts;
      first, second, and third output gears operably coupled to the main drive gear and configured to rotate in response to a rotation of the main drive gear;
      a selector cam; and
      a selector motor operably coupled to the selector cam and configured to move the selector cam relative to the first, second, and third output shafts between a first position, in which the first output shaft is non-rotatably coupled to the first output gear, a second position, in which the second output shaft is non-rotatably coupled to the second output gear, and a third position in which the third output shaft is non-rotatably coupled to the third output gear.

2. The handle assembly according to claim 1, wherein the transmission assembly further includes:
- a first coupling shaft non-rotatably coupled to the first output shaft;
- a second coupling shaft non-rotatably coupled to the second output shaft; and
- a third coupling shaft non-rotatably coupled to the third output shaft, wherein the first coupling shaft is configured to translate into non-rotatable engagement with the first output gear when the selector cam is moved to the first position such that only the first output shaft rotates in response to a rotation of the main drive gear when the selector cam is in the first position, wherein the second coupling shaft is configured to translate into non-rotatable engagement with the second output gear when the selector cam is moved to the second position such that only the second output shaft rotates in response to the rotation of the main drive gear when the selector cam is in the second position, and wherein the third coupling shaft is configured to translate into non-rotatable engagement with the third output gear when the selector cam is moved to the third position such that only the third output shaft rotates in response to the rotation of the main drive gear when the selector cam is in the third position.

3. The handle assembly according to claim 2, wherein the first, second, and third coupling shafts are each resiliently biased toward a proximal position in which the first, second, and third coupling shafts are respectively non-rotatably engaged with the first, second, and third output gears, the selector cam being configured to selectively maintain only one of the first, second, or third coupling shafts in a distal position and out of non-rotatable engagement with the respective first, second, and third output gears.

4. The handle assembly according to claim 3, wherein the selector cam has a distal-facing surface configured to engage and maintain a selected one of the first, second, or third coupling shafts in the distal position.

5. The handle assembly according to claim 1, wherein the transmission assembly further includes a first coupling shaft non-rotatably coupled to the first output shaft, wherein the first coupling shaft is configured to translate into non-rotatable engagement with the first output gear when the selector cam is moved to the first position such that only the first output shaft rotates in response to a rotation of the main drive gear when the selector cam is in the first position.

6. The handle assembly according to claim 5, wherein the first coupling shaft extends through the first output gear and is slidable therein between a proximal position, in which the first coupling shaft is non-rotatably engaged with the first output gear, and a distal position, in which the first coupling shaft is disengaged from the first output gear.

7. The handle assembly according to claim 6, wherein the first coupling shaft has a proximal end portion engaged with the selector cam, and a distal end portion having a gear, the first output gear having a geared inner surface configured to meshingly engage with the gear of the distal end portion of the first coupling shaft when the first coupling shaft is in the proximal position.

8. The handle assembly according to claim 1, wherein the selector motor rotatably supports and drives a gear, the selector cam having a plurality of teeth in meshing engagement with the gear of the selector motor and configured to move the selector cam between the first, second, and third positions.

9. The handle assembly according to claim 8, wherein the selector cam has an arcuate shape and is configured to rotate around the main drive motor between the first, second, and third positions.

* * * * *